United States Patent
Tawara et al.

(10) Patent No.: US 11,786,135 B2
(45) Date of Patent: *Oct. 17, 2023

(54) BLOOD PRESSURE INFORMATION MEASURING DEVICE

(71) Applicant: OMRON HEALTHCARE CO., LTD., Muko (JP)

(72) Inventors: Chisato Tawara, Kyoto (JP); Minoru Taniguchi, Kyoto (JP); Keita Ikeda, Kyoto (JP); Hirotaka Hayashi, Kyoto (JP); Masaki Harada, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 606 days.

This patent is subject to a terminal disclaimer.

(21) Appl. No.: 16/535,615

(22) Filed: Aug. 8, 2019

(65) Prior Publication Data

US 2019/0357783 A1 Nov. 28, 2019

Related U.S. Application Data

(63) Continuation of application No. PCT/JP2017/047056, filed on Dec. 27, 2017.

(30) Foreign Application Priority Data

Feb. 16, 2017 (JP) ................................. 2017-027193

(51) Int. Cl.
  *A61B 5/022* (2006.01)
  *A61B 5/0225* (2006.01)
  *A61B 5/0235* (2006.01)

(52) U.S. Cl.
  CPC ........ *A61B 5/02233* (2013.01); *A61B 5/0225* (2013.01); *A61B 5/0235* (2013.01); *A61B 5/02225* (2013.01)

(58) Field of Classification Search
  CPC ............ A61B 5/02233; A61B 5/02225; A61B 5/0225; A61B 5/0235; A61B 5/6824; A61B 5/023; A61B 5/02208
  See application file for complete search history.

(56) References Cited

U.S. PATENT DOCUMENTS

| 5,660,182 | A | * | 8/1997 | Kuroshaki | ......... | A61B 5/02233 |
| | | | | | | 600/499 |
| 6,336,901 | B1 | * | 1/2002 | Itonaga | .............. | A61B 5/02141 |
| | | | | | | 600/499 |

(Continued)

FOREIGN PATENT DOCUMENTS

| JP | 2011-177249 A | 9/2011 |
| JP | 2012-147995 A | 8/2012 |

(Continued)

OTHER PUBLICATIONS

Mar. 27, 2018 International Search Report issued in International Application No. PCT/JP2017/047056.

*Primary Examiner* — Andrey Shostak
(74) *Attorney, Agent, or Firm* — Oliff PLC

(57) ABSTRACT

A blood pressure information measurement device, including first and second fluid bags in the first fluid bag; a pressure mechanism increases/decreases pressure in an internal space of the first fluid bag and the pressure in the internal space of the second bag; a control unit controls operation of the pressure mechanism; a pressure detection device detects an internal pressure of the first and the second fluid bag; and a calculation unit that calculates blood pressure information detected by the device. In calculating blood pressure information, the control unit controls operation of the pressure increase/reduction mechanism after the internal space of one fluid bag of the first and second fluid bags pressurized and expanded until internal pressure of one fluid bag reaches a predetermined pressure, the internal space of the other fluid (Continued)

bag of the first and second fluid bags pressurized and expanded while the one bag is kept sealed.

4 Claims, 9 Drawing Sheets

(56) References Cited

U.S. PATENT DOCUMENTS

| | | | | |
|---|---|---|---|---|
| 2005/0240109 A1* | 10/2005 | Inoue | .................... | A61B 5/021 |
| | | | | 600/499 |
| 2005/0251052 A1* | 11/2005 | Sano | ................. | A61B 5/02233 |
| | | | | 600/490 |
| 2012/0240377 A1* | 9/2012 | Ashida | ............... | A61B 5/02233 |
| | | | | 29/428 |

FOREIGN PATENT DOCUMENTS

| | | | |
|---|---|---|---|
| JP | 2012147995 A * | 8/2012 | |
| WO | 2009/145027 A1 | 12/2009 | |
| WO | 2014/102873 A1 | 7/2014 | |
| WO | WO-2014102873 A1 * | 7/2014 | ......... A61B 5/02233 |

\* cited by examiner

BLOOD PRESSURE INFORMATION MEASURING DEVICE

TECHNICAL FIELD

The present invention relates to a blood pressure information measurement device for measuring blood pressure information and more particularly relates to a blood pressure information measurement device capable of measuring blood pressure information by using a fluid bag and compressing a living body.

BACKGROUND ART

Measuring blood pressure information is very important in knowing the health state of a subject. Systolic blood pressure values (hereinafter referred to as systolic blood pressure), diastolic blood pressure values (hereinafter referred to as diastolic blood pressure), and the like are widely known as representative indicators in health management and known for their usefulness. In recent years, as well as systolic blood pressure and diastolic blood pressure, measuring pulse waves has also been used to find the cardiac load, degree of arteriosclerosis, and the like.

A blood pressure information measurement device is a device for obtaining indicators for health management based on the measured blood pressure information. There is a demand for such devices to have further application in fields such as the early detection, prevention, and treatment of circulatory system diseases. Note that the blood pressure information includes a broad range of information relating to the circulatory system including various indicators for indicating the systolic blood pressure, the diastolic blood pressure, the mean blood pressure, the pulse wave, the pulse, and the degree of arteriosclerosis.

Generally, a cuff for a blood pressure information measurement device (hereinafter, also referred to simply as cuff) is used to measure blood pressure information. Here, "cuff" refers to a band-like or annular structure that includes a fluid bag with an empty space inside and is capable of being worn on a portion of the body, the cuff being used to measure blood pressure information via a gaseous or liquid fluid being inserted into the empty space to expand the fluid bag and being released to contract the fluid bag. Note that, cuffs are also referred to as arm bands or manschettes.

Typically, the cuff is wrapped around a measurement site (e.g., the upper arm) in the length direction of the cuff. If the length of the cuff in the width direction (length in the direction orthogonal to the length direction, i.e., cuff width) does not match the thickness of the measurement site, accurate blood pressure measurements may not be possible.

The literatures disclosing a blood pressure information measurement device that determines a thickness of a measurement site and measures blood pressure information include, for example, JP 2012-147995 A (Patent Document 1).

The blood pressure information measurement device described in Patent Document 1 includes a cuff for a blood pressure information measurement device that includes a first air bag and a second air bag contained in the first air bag. When using the blood pressure information measurement device to measure blood pressure information, the user enters in advance whether the measurement site is thick or thin. Then, the blood pressure information measurement device pressurizes the first air bag or the second air bag in accordance with the entered information. In a case where thick is entered, the first air bag is pressurized, and in a case where thin is entered, the second air bag is pressurized.

When either of the first air bag or the second air bag is pressurized, the time taken to reach a predetermined reference pressure (P1 when the first air bag is pressurized and P2 when the second air bag is pressurized) is measured. In a case where the time taken is less than a preset threshold (Th1 when the first air bag is pressurized and Th2 when the second air bag is pressurized), a determination unit determines the measurement site to be thin, and in a case where the time taken is longer than the preset threshold, the determination unit determines the measurement site to be thick.

In a case where the determination of the determination unit and the initially entered information match, either of the first air bag or the second air bag pressurized in accordance with the entered information is continuously pressurized and the blood pressure information is measured. In a case where the determination of the determination unit and the initially entered information do not match, the pressurization of either of the first air bag or the second air bag pressurized in accordance with the entered information is ceased, the other first air bag or second air bag is pressurized, and the blood pressure information is measured.

CITATION LIST

Patent Literature

Patent Document 1: JP 2012-147995 A

SUMMARY OF INVENTION

Technical Problem

In the cuff for the blood pressure information measurement device described in Patent Document 1, as described above, in a case where the user in advance enters "thick" for the measurement site and the determination unit determines that the measurement site is "thick", the blood pressure information is measured by pressurizing only the first air bag. Accordingly, a significant amount of air is supplied to the first air bag, making it difficult to clearly detect the pulse waves of the user. Thus, measurement accuracy is decreased.

In a case where the user in advance enters "thin" for the measurement site and the determination unit determines that the measurement site is "thin", the blood pressure information is measured by pressurizing only the second air bag. When the second air bag, which is accommodated in the first air bag, is expanded without expanding the first air bag, the outer surface of the second air bag and the inner surface of the first air bag rub against one another. As a result, the second air bag may not smoothly expand. The friction between the first air bag and the second air bag produces noise that is superimposed on the detection value of the pressure sensor. As a result, measurement accuracy is decreased.

The present invention has been made in view of the problems described above, and an object of the present invention is to provide a blood pressure information measurement device with improved measurement accuracy that includes a first fluid bag and a second fluid bag accommodated in the first fluid bag.

Solution to Problem

A blood pressure information measurement device according to an aspect of the present invention includes, a cuff including a first fluid bag configured to expand and contract by a fluid entering and exiting the first fluid bag, and a second fluid bag accommodated in the first fluid bag and configured to expand and contract by a fluid entering and exiting the second fluid bag, a pressure increase/reduction mechanism configured to increase and decrease a pressure in an internal space of the first fluid bag and a pressure in an internal space of the second fluid bag, a control unit configured to control operation of the pressure increase/reduction mechanism, a pressure detection device configured to detect an internal pressure of the first fluid bag and an internal pressure of the second fluid bag, and a calculation unit configured to calculate blood pressure on the basis of pressure information detected by the pressure detection device with the cuff being worn at a measurement site. In calculating blood pressure information using the pressure detection device and the calculation unit, the control unit controls operation of the pressure increase/reduction mechanism such that after the internal space of one fluid bag of the first fluid bag and the second fluid bag is pressurized and expanded until an internal pressure of the one fluid bag reaches a predetermined pressure, the internal space of the other fluid bag of the first fluid bag and the second fluid bag is pressurized and expanded while the one fluid bag is kept sealed.

In the blood pressure information measurement device according to an aspect of the present invention, the pressure increase/reduction mechanism, after the internal space of the second fluid bag is pressurized and the internal pressure of the second fluid bag reaches a second pressure, may pressurize the internal space of the first fluid bag while the second fluid bag is kept sealed.

In the blood pressure information measurement device according to an aspect of the present invention, the pressure increase/reduction mechanism may include a first pressure pump and a second pressure pump. In this case, preferably, the first pressure pump pressurizes the internal space of the first fluid bag, and the second pressure pump pressurizes the internal space of the second fluid bag. Furthermore, in this case, the control unit, after the second pressure pump is driven with the first pressure pump being stopped, may control operation of the pressure increase/reduction mechanism to drive the first pressure pump with the second pressure pump being stopped.

In the blood pressure information measurement device according to an aspect of the present invention, the pressure increase/reduction mechanism may include a single pressure pump, a fluid supply path, and a switching valve. In this case, preferably, the pressure pump pressurizes the internal space of the first fluid bag and the internal space of the second fluid bag; and preferably, an end on a first side of the fluid supply path is connected to the pressure pump, and an end on a second side of the fluid supply path branches into a first supply path connected to the first fluid bag and a second supply path connected to the second fluid bag. Furthermore, preferably, the switching valve is provided at a point along the fluid supply path and switches between a state in which a fluid is supplied to the first fluid bag via the first supply path and a state in which a fluid is supplied to the second fluid bag via the second supply path. In this case, the control unit, by controlling operation of the pressure pump and the switching valve, after the internal space of the second fluid bag is pressurized via the fluid supplied via the second supply path, may pressurize the internal space of the first fluid bag via the fluid supplied via the first supply path.

In the blood pressure information measurement device according to an aspect of the present invention, after the internal space of the first fluid bag is pressurized and the internal pressure of the first fluid bag reaches a first pressure, the pressure increase/reduction mechanism may pressurize the internal space of the second fluid bag while the first fluid bag is kept sealed.

In the blood pressure information measurement device according to an aspect of the present invention, the pressure increase/reduction mechanism may include a first pressure pump and a second pressure pump. In this case, preferably, the first pressure pump pressurizes the internal space of the first fluid bag, and the second pressure pump pressurizes the internal space of the second fluid bag. Furthermore, in this case, the control unit, after the first pressure pump is driven with the second pressure pump being stopped, may control operation of the pressure increase/reduction mechanism to drive the second pressure pump with the first pressure pump being stopped.

In the blood pressure information measurement device according to an aspect of the present invention, the pressure increase/reduction mechanism may include a single pressure pump, a fluid supply path, and a switching valve. In this case, preferably, the pressure pump pressurizes the internal space of the first fluid bag and the internal space of the second fluid bag; and preferably, an end on a first side of the fluid supply path is connected to the pressure pump, and an end on a second side of the fluid supply path branches into a first supply path connected to the first fluid bag and a second supply path connected to the second fluid bag. Furthermore, preferably, the switching valve is provided at a point along the fluid supply path and switches between a state in which a fluid is supplied to the first fluid bag via the first supply path and a state in which a fluid is supplied to the second fluid bag via the second supply path. In this case, the control unit, by controlling operation of the pressure pump and the switching valve, after the internal space of the first fluid bag is pressurized via the fluid supplied via the first supply path, may pressurize the internal space of the second fluid bag via the fluid supplied via the second supply path.

Advantageous Effects of Invention

According to an aspect of the present invention, a blood pressure information measurement device with improved measurement accuracy that includes a first fluid bag and a second fluid bag accommodated in the first fluid bag can be provided.

DESCRIPTION OF EMBODIMENTS

Figure 1:
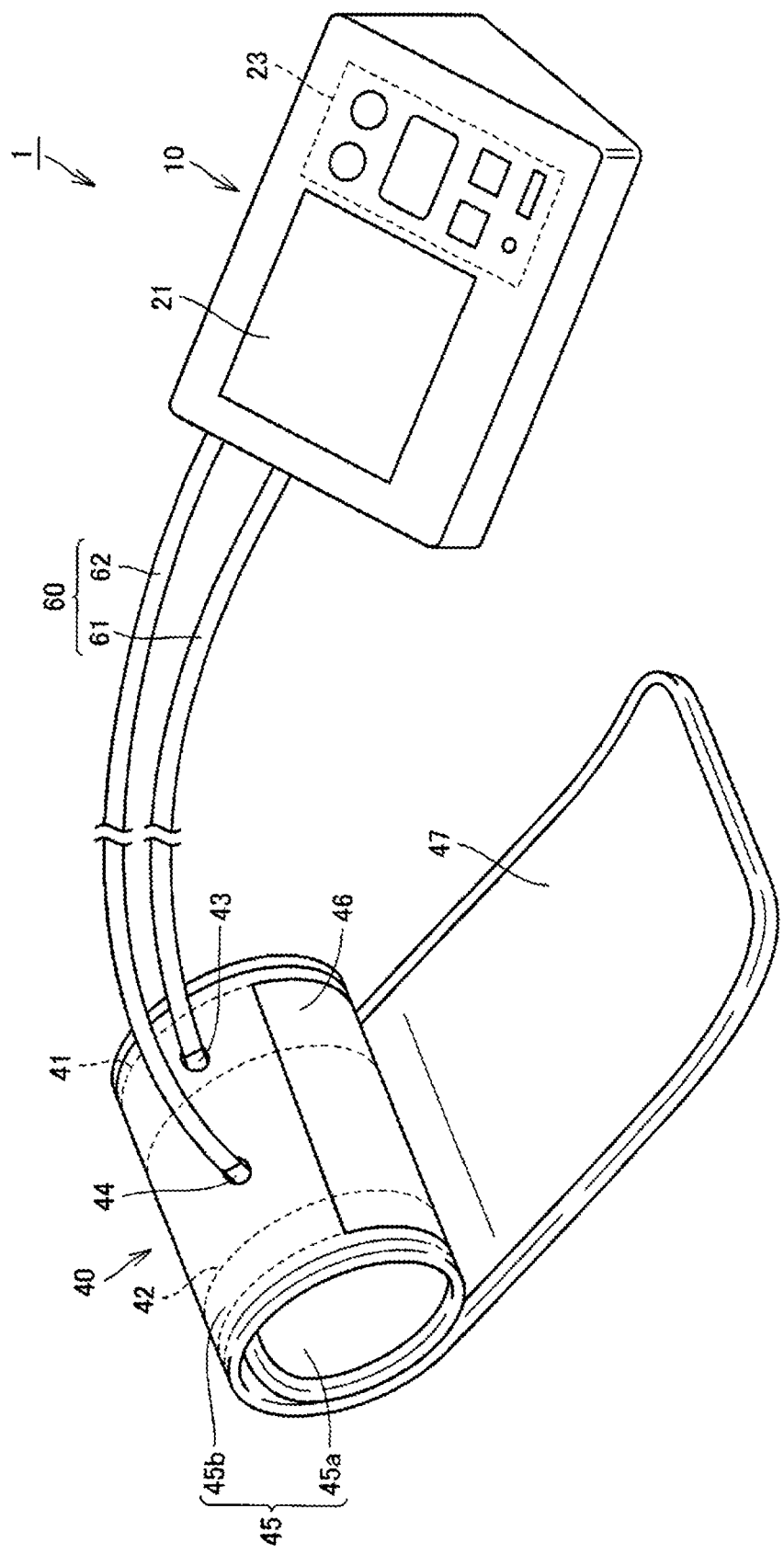
FIG. 1 is a perspective view illustrating an appearance and a structure of a blood pressure monitor according to a first embodiment.

Embodiments of the present invention will be described in detail below with reference to the drawings. In the embodiments described below, a cuff for a blood pressure used in an upper arm blood pressure monitor that is configured to be capable of measuring blood pressure values including the systolic blood pressure and the diastolic blood pressure is used as an example of a cuff for a blood pressure information measurement device. Note that in the following, identical or similar components are given the same reference signs in the drawings, and the descriptions thereof are not repeated.

First Embodiment

FIG. 1 is a perspective view illustrating an appearance and a structure of a blood pressure monitor according to a first embodiment. A schematic configuration of a blood pressure monitor 1 according to the first embodiment will be described with reference to FIG. 1.

As illustrated in FIG. 1, the blood pressure monitor 1 includes a body 10, a cuff 40, and an air tube 60 as a fluid supply path. The air tube 60 connects the body 10 and cuff 40, which are configured separately.

The air tube 60 includes a first air tube 61 as a first supply path and a second air tube 62 as a second supply path. The first air tube 61 and the second air tube 62 are separated from each other, for example. The first air tube 61 and the second air tube 62 are each constituted by a flexible tube made of resin, for example.

The body 10 includes a box-like casing and includes a display unit 21 and an operation unit 23 on a top surface thereof. The body 10 is placed on a placement surface of a table and the like when measurement is performed.

The cuff 40 has a band-like shape allowing it to be wrapped around the upper arm, i.e., the site where it is worn. The cuff 40 is worn on the upper arm when measurement is performed. When wrapped around the upper arm in the worn state, the cuff 40 takes an annular form. The cuff 40 includes an outer cover 45, a first air bag 41 as a first fluid bag, and a second air bag 42 as a second fluid bag. Details of the first air bag 41 and the second air bag 42 will be described later using FIGS. 2 and 3.

The outer cover 45 has a bag-like shape and a band-like shape that is substantially rectangular in a plan view when the outer cover 45 is unfolded. The outer cover 45 includes an outer cover member 45b that is located radially outward when in a worn state, and an inner cover member 45a that is located radially inward and is in contact with the surface of the upper arm when in a worn state.

The outer cover 45 is formed in a bag-like shape by the outer cover member 45b and the inner cover member 45a being layered on one another, with the edges being covered by a bias tape (not illustrated), and joined (for example, by sewing, welding, or the like).

A surface fastener 46 is provided on the outer circumferential surface of the outer cover 45 at/near a first end in the longitudinal direction, and a surface fastener 47 is provided on an inner circumferential surface of the outer cover 45 at/near a second end on the opposite side from the first end. The surface fastener 46 is constituted by a hook fastener, for example, and the surface fastener 47 is constituted by a loop fastener, for example.

The surface fasteners 46, 47 are configured to fasten together when the outer cover 45 is wrapped around the upper arm by the section of the outer cover 45 at/near the first end and the section of the outer cover 45 at/near the second end being layered on one another on the surface of the upper arm. Thus, by fastening together the surface fasteners 46, 47 with the cuff 40 wrapped around the upper arm, the outer cover 45 is fixed on the upper arm in the worn state.

Figure 2:
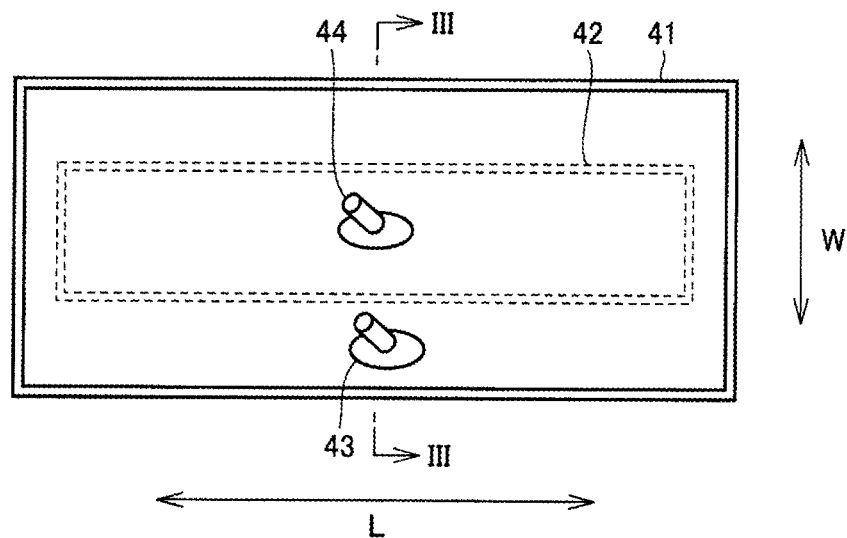
FIG. 2 is a developed view of the first air bag and the second air bag according to the first embodiment.
Figure 3:
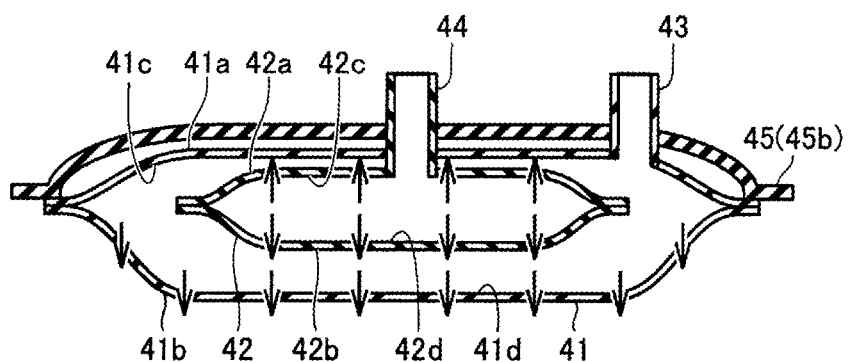
FIG. 3 is a cross-sectional view illustrating the first air bag and the second air bag illustrated in FIG. 2 in a pressurized state.

FIG. 2 is a developed view of the first air bag and the second air bag according to the first embodiment. FIG. 3 is a cross-sectional view illustrating the first air bag and the second air bag illustrated in FIG. 2 in a pressurized state. Note that FIG. 3 is a cross-sectional view corresponding to the section along the line III-III illustrated in FIG. 2. The first air bag 41 and the second air bag 42 will be described with reference to FIGS. 2 and 3.

As illustrated in FIG. 2, the first air bag 41 has a bag-like shape and a band-like shape that is substantially rectangular in a plan view when the first air bag 41 is unfolded. The first air bag 41 includes a length direction L that corresponds to the circumferential direction when the first air bag 41 is wrapped at the measurement site and a width direction W orthogonal to the length direction L.

The first air bag 41 includes a pair of outer surfaces 41a, 41b and a pair of inner surfaces 41c, 41d.

A first nipple 43 is provided on the outer surface 41a of the pair of outer surfaces 41a, 41b. The first air bag 41 expands and contracts by air entering and exiting via the first nipple 43.

The second air bag 42 has a bag-like shape and a band-like shape that is substantially rectangular in a plan view when the second air bag 42 is unfolded. The shape of the second air bag 42 is smaller than the shape of the first air bag 41. The second air bag 42 is accommodated in the first air bag 41. The second air bag 42 is centrally positioned in the length direction of the first air bag 41 in a state in which the first air bag 41 and the second air bag 42 are both unfolded flat.

The second air bag 42 includes a pair of outer surfaces 42a, 42b and a pair of inner surfaces 42c, 42d. The pair of outer surfaces 42a, 42b of the second air bag 42 are disposed facing the pair of inner surfaces 41c, 41d of the first air bag 41.

A second nipple 44 is provided on the outer surface 42a of the pair of outer surfaces 42a, 42b. The second air bag 42 expands and contracts by air entering and exiting via the second nipple 44.

The second nipple 44 is roughly centrally disposed in the length direction L and the width direction W of the second air bag 42, for example. By disposing the second nipple 44 in such a position, the second air bag 42 can be expanded in a roughly uniform manner.

When the first air bag 41 and the second air bag 42 are unfolded flatly, the first nipple 43 is preferably disposed at a position corresponding to the outer edge section of the second air bag 42 or a position further outward than the outer edge section.

Here, a position corresponding to the outer edge section of the second air bag 42 or a position further outward than the outer edge section is a position such that the first nipple 43 is not blocked by the second air bag 42 in an insertion state when the first air bag 41 is not expanded and the second air bag 42 is expanded. Accordingly, "a position corresponding to the outer edge section of the second air bag 42" includes not only a position overlapping with the outer edge section of the second air bag 42, but also a position a certain amount inward from the outer edge section of the second air bag 42 in a plan view when the first air bag 41 and the second air bag 42 are unfolded.

Also, when the first air bag 41 and the second air bag 42 are unfolded flatly, the first nipple 43 is preferably disposed side by side with the second nipple 44 in a direction parallel with the width direction W of the first air bag 41.

In the first embodiment, when the first air bag 41 and the second air bag 42 are unfolded flatly, the first nipple 43 is disposed at a position outward from the outer edge section of the second air bag, side by side with the second nipple 44 in a direction parallel with the width direction of the first air bag 41.

The second nipple 44 extends outside through the inner surface 41c of the first air bag 41 disposed facing the outer surface 42a of the second air bag 42.

The first air bag 41 and the second air bag 42 are each preferably constituted by a bag-like member formed using a resin sheet. The material of the resin sheet constituting the first air bag 41 and the second air bag 42 can be any material that is highly elastic and can prevent air from leaking from the internal space. From this perspective, suitable materials for the resin sheet include ethylene-vinyl acetate copolymers, soft vinyl chloride, polyurethane, polyamide, and the like.

As illustrated in FIG. 3, when blood pressure is measured, the internal space of both the first air bag 41 and the second air bag 42 is pressurized and expanded. As described below, the internal space of the first air bag 41 may be pressurized first, or the internal space of the second air bag 42 may be pressurized first.

As described above, when the first air bag 41 and the second air bag 42 are unfolded flatly, the first nipple 43 is disposed at a position corresponding to the outer edge section of the second air bag 42 or a position further outward than the outer edge section. Thus, in the case of the second air bag 42 being filled with air and expanded before the first air bag 41, the first nipple 43 can be prevented from being blocked by the second air bag 42. This allows air to be reliably introduced inside the first nipple 43.

Additionally, by pressurizing the internal space of the second air bag 42, in accordance with Pascal's principle, even in a case of a small amount of air being supplied to the first air bag 41, the force of the first air bag 41 pressing against the measurement site can be amplified.

Figure 4:
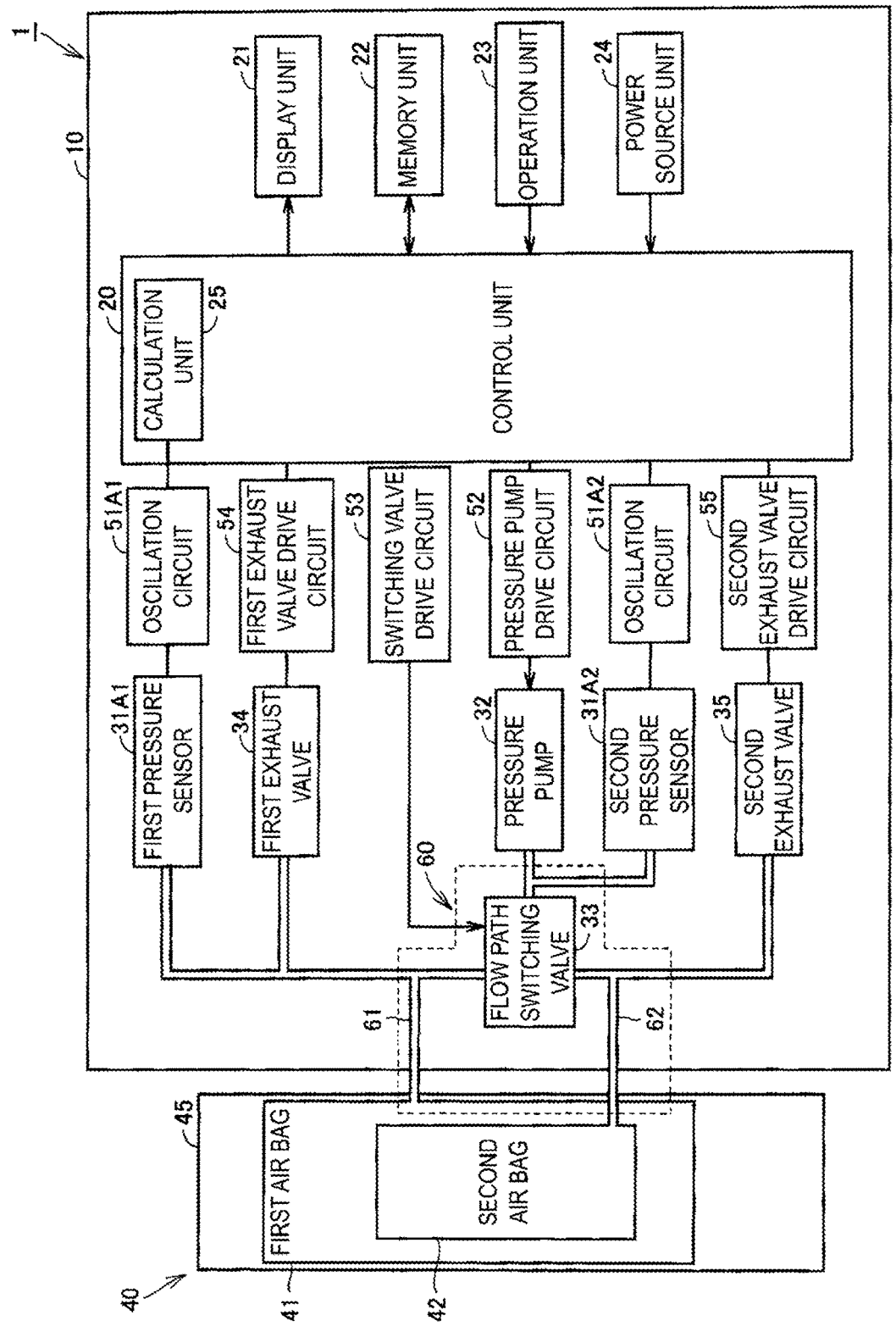
FIG. 4 is a functional block diagram illustrating the configuration of the blood pressure monitor according to the first embodiment.

FIG. 4 is a functional block diagram illustrating the configuration of the blood pressure monitor according to the first embodiment. The functional blocks of the blood pressure monitor 1 will be described with reference to FIG. 4.

As illustrated in FIG. 4, in addition to the display unit 21 and the operation unit 23 described above, the body 10 includes a control unit 20, a memory unit 22, a power source unit 24, a first pressure P1 sensor 31A1 and a second pressure P2 sensor 31A2 as pressure detection devices, a pressure pump 32, a flow path switching valve 33 as a switching valve, a first exhaust valve 34, a second exhaust valve 35, an oscillation circuit 51A1, an oscillation circuit 51A2, a pressure pump drive circuit 52, a switching valve drive circuit 53, a first exhaust valve drive circuit 54, and a second exhaust valve drive circuit 55.

The pressure pump 32, the flow path switching valve 33, the first exhaust valve 34, and the second exhaust valve 35 correspond to a pressure increase/reduction mechanism that increases or decreases the pressure in the internal space of the first air bag 41 and the second air bag 42.

The pressure increase/reduction mechanism is configured to be switchable from a first state to a second state. In the first state, the internal space of the one fluid bag of the first air bag 41 and the second air bag 42 is pressurized and expanded. In the second state, the one fluid bag of the first air bag 41 and the second air bag 42 is kept sealed and the internal space of the other fluid bag of the first air bag 41 and the second air bag 42 is pressurized and expanded.

The control unit 20 is constituted by a central processing unit (CPU) and, for example, is configured to comprehensively control the blood pressure monitor 1. The control unit 20 includes a calculation unit 25 that calculates the blood pressure on the basis of the pressure information detected by the first pressure P1 sensor 31A1 when the cuff 40 is worn on the upper arm at the measurement site.

The memory unit 22 is constituted by read-only memory (ROM) and/or random-access memory (RAM) and, for example, is configured to store a program for causing the control unit 20 and the like to execute a processing procedure for measuring blood pressure values and store measurement results and the like.

The display unit 21 is constituted by a liquid crystal display (LCD) and, for example, is configured to display measurement results and the like. The operation unit 23 is configured to receive an operation by a user or the like and input the instruction from the outside into the control unit 20 and the power source unit 24. The power source unit 24 is configured to supply power to the control unit 20.

The control unit 20 inputs control signals for driving the pressure pump 32, the flow path switching valve 33, the first exhaust valve 34, and the second exhaust valve 35 into the pressure pump drive circuit 52, the switching valve drive circuit 53, the first exhaust valve drive circuit 54, and the second exhaust valve drive circuit 55. Additionally, the control unit 20 inputs the blood pressure value calculated by the calculation unit 25 into the memory unit 22 and the display unit 21 as a measurement result.

Note that the blood pressure monitor 1 may separately include an output unit configured to output the blood pressure value as a measurement result to an external device (for example, a personal computer (PC), a printer, or the like). For example, a serial communication line, a writing device that writes to various types of recording medium, or the like can be used as the output unit.

The pressure pump 32 pressurizes the internal space of the first air bag 41 and the internal space of the second air bag 42 by supplying air to the internal space of the first air bag 41 and the second air bag 42. The pressure pump 32 supplies air to the first air bag 41 and the second air bag 42 via the air tube 60. An end on a first side of the air tube 60 is connected to the pressure pump 32. An end on a second side of the air tube 60 branches into the first air tube 61 connected to the first air bag 41 and the second air tube 62 connected to the second air bag 42.

The end of the first air tube 61 is inserted into the first nipple 43 and connected to the first air bag 41. The end of the second air tube 62 is inserted into the second nipple 44 and connected to the second air bag 42.

The pressure pump drive circuit 52 controls the operation of the pressure pump 32 on the basis of a control signal received from the control unit 20.

The flow path switching valve 33 is provided at a point along the air tube 60. Specifically, the flow path switching valve 33 is provided at a branching section that branches into the first air tube 61 and the second air tube 62. The flow path switching valve 33 switches between a state in which air is supplied to the first air bag 41 via the first air tube 61 (a state in which the internal space of the first air bag 41 is pressurized) and a state in which air is supplied to the second air bag 42 via the second air tube 62 (a state in which the internal space of the second air bag 42 is pressurized).

The switching valve drive circuit 53 controls the operation of the flow path switching valve 33 on the basis of a control signal received from the control unit 20.

The first exhaust valve 34 is connected to the first air tube 61. By opening/closing the first exhaust valve 34, the internal pressure of the first air bag 41 is maintained or the internal space of the first air bag 41 is opened to the outside to reduce the internal pressure of the first air bag 41.

The first exhaust valve drive circuit 54 controls the operation of the first exhaust valve 34 on the basis of a control signal received from the control unit 20.

The second exhaust valve 35 is connected to the second air tube 62. By opening/closing the second exhaust valve 35, the internal pressure of the second air bag 42 is maintained or the internal space of the second air bag 42 is opened to the outside to reduce the internal pressure of the second air bag 42.

The second exhaust valve drive circuit 55 controls the operation of the second exhaust valve 35 on the basis of a control signal received from the control unit 20.

The internal pressure of the first air bag 41 can be measured using the first pressure P1 sensor 31A1. The internal pressure of the second air bag 42 can be measured using the second pressure P2 sensor 31A2. The first pressure P1 sensor 31A1 and the second pressure P2 sensor 31A2 are capacitive sensors.

The capacitance of the first pressure P1 sensor 31A1 varies depending on the internal pressure of the first air bag 41. The oscillation circuit 51A1 generates a signal having an oscillation frequency in accordance with the capacitance of the first pressure P1 sensor 31A1 and inputs the generated signal to the control unit 20.

The capacitance of the second pressure P2 sensor 31A2 varies depending on the internal pressure of the second air bag 42. The oscillation circuit 51A2 generates a signal having an oscillation frequency in accordance with the capacitance of the second pressure P2 sensor 31A2 and inputs the generated signal to the control unit 20.

Figure 5:
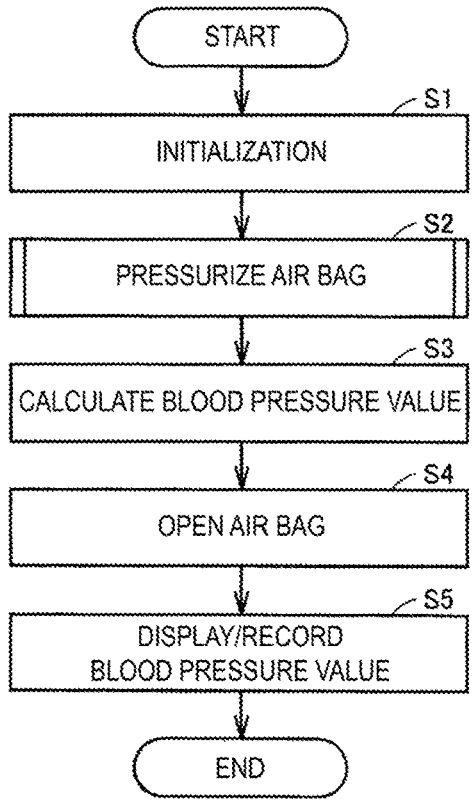
FIG. 5 is a flow chart illustrating the measurement flow of the blood pressure monitor according to the first embodiment.

FIG. 5 is a flow chart illustrating the measurement flow of the blood pressure monitor according to the first embodiment. The measurement flow of the blood pressure monitor 1 will be described with reference to FIG. 5.

When measuring blood pressure values, the cuff 40 is wrapped around the upper arm of the subject and worn in advance. In this state, when the operation unit 23 provided in the body 10 is operated and the blood pressure monitor 1 is turned on, power is supplied to the control unit 20 from the power source unit 24 to drive the control unit 20.

As illustrated in FIG. 5, after the control unit 20 is driven, the control unit 20 first initializes the blood pressure monitor 1 (step S1). In the initialization, the control unit 20 causes the first air bag 41 and the second air bag 42 to be in an open state in which the internal space of the first air bag 41 and the second air bag 42 is opened to the outside by controlling the operation of the first exhaust valve 34 and the second exhaust valve 35.

Next, the control unit 20 waits for an instruction to start the measurement, and when the operation unit 23 is operated and the instruction to start the measurement is input, the control unit 20 causes the first exhaust valve 34 and the second exhaust valve 35 to be closed and starts driving the pressure pump 32 (step S2).

In step S2, the control unit 20 controls the operation of the flow path switching valve 33 such that air is supplied to one of the first air bag 41 and the second air bag 42. When the internal pressure of the first air bag 41 and the second air bag 42 reaches a prescribed pressure, the control unit 20 controls the operation of the flow path switching valve 33 such that air is supplied to the other of the first air bag 41 and the second air bag 42. The operation of step S2 will be described in details below with reference to FIGS. 6 to 9.

Note that "predetermined pressure" is the first pressure P1 (see FIG. 7) in the case of the internal space of the first air bag 41 being pressurized first and is the second pressure P2 (see FIG. 9) in the case of the internal space of the second air bag 42 being pressurized first. In this case, the first pressure P1 is less than the second pressure P2.

In the process of pressurizing, the control unit 20 calculates the systolic blood pressure and the diastolic blood pressure by using a known procedure (step S3). Specifically, in the process of increasing the internal pressure of both the first air bag 41 and the second air bag 42, the control unit 20 obtains the internal pressure of the first air bag 41 from the oscillation frequency obtained from the oscillation circuit 51A1 and extracts the pulse wave information superimposed on the obtained internal pressure of the first air bag 41. Then, the control unit 20 calculates the blood pressure value on the basis of the extracted pulse wave information.

When the blood pressure value is calculated in step S3, the control unit 20 stops driving the pressure pump 32 and opens the first exhaust valve 34 and the second exhaust valve 35 to completely exhaust the air in the first air bag 41 and the second air bag 42 (step S4).

Additionally, the blood pressure value is displayed on the display unit 21 as the measurement result, and the blood pressure value is stored in the memory unit 22 (step S5).

Thereafter, the control unit 20 waits for an instruction to power off, and when the operation unit 23 is operated and an instruction to power off is input, the control unit 20 blocks the supply of power from the power source unit 24 to the control unit 20, and the sequence of processing procedures is ended.

Figure 6:
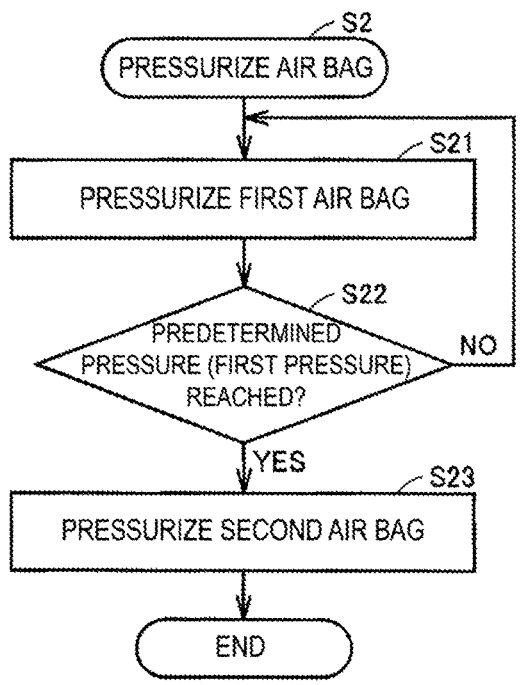
FIG. 6 is a flow chart illustrating a first example of the step of pressurizing the air bag indicated in FIG. 5.
Figure 7:
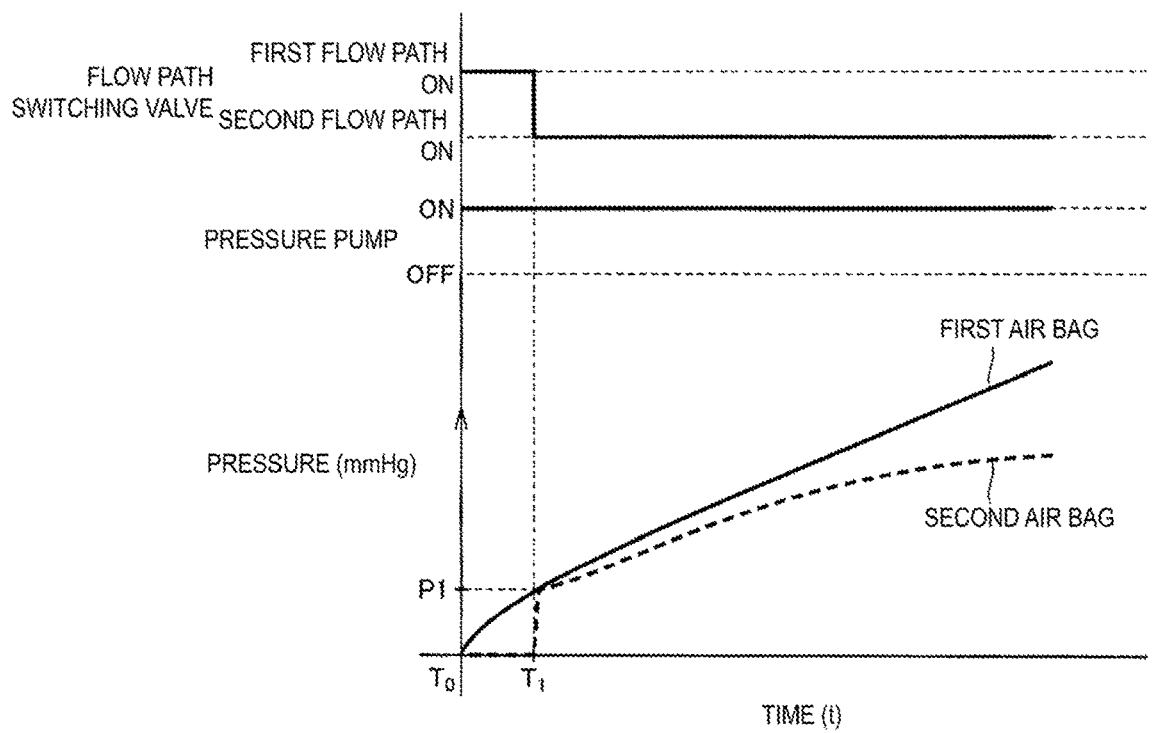
FIG. 7 is a diagram illustrating change in the operating state of a flow path switching valve and a pressure pump and change in the internal pressure of the first air bag and the second air bag, in accordance with the first example indicated in FIG. 6.

FIG. 6 is a flow chart illustrating a first example of the step of pressurizing the air bag indicated in FIG. 5. FIG. 7 is a diagram illustrating change in the operating state of the flow path switching valve and the pressure pump and change in the internal pressure of the first air bag and the second air bag, in accordance with the first example indicated in FIG. 6 The first example of the step of pressurizing the air bag will be described with reference to FIGS. 6 and 7.

As illustrated in FIGS. 6 and 7, in the first example of the step of pressurizing the air bag (step S2), firstly the first air bag 41 is pressurized (step S21). Specifically, the operation of the flow path switching valve 33 is controlled to close the second air tube 62 side and connect the first air tube 61 and the pressure pump 32. This allows air to be supplied to the first air bag 41 via the first air tube 61. In this state, the pressure pump 32 is driven and air is supplied to the first air bag 41 via the first air tube 61, and the internal space of the first air bag 41 is pressurized.

Next, the control unit 20 determines whether or not the internal pressure of the first air bag 41 has reached a predetermined pressure (the first pressure P1) on the basis of the pressure information of the first air bag 41 detected by the first pressure P1 sensor 31A1 (step S22). In accordance with a determination that the internal pressure of the first air bag 41 is less than the predetermined pressure (step S22: NO), pressurization of the internal space of the first air bag 41 continues until the internal pressure of the first air bag 41 reaches the first pressure P1. Note that the first pressure P1 is approximately 50 mmHg, for example.

In accordance with a determination that the internal pressure of the first air bag 41 has reached the first pressure P1 (step S22: YES), the internal space of the second air bag 42 is pressurized (step S23). In the present embodiment, the pressurization of the internal space of the first air bag 41 starts at T0, and the internal pressure of the first air bag 41 reaches the first pressure P1 at T1.

In the step of pressurizing the second air bag 42, via the flow path switching valve 33, the first air tube 61 side is closed and the second air tube 62 and the pressure pump 32 are connected. This allows air to be supplied to the second air bag 42 via the second air tube 62. In this state, the first air bag 41 is kept sealed by the first exhaust valve 34 being kept in a closed state.

As illustrated in FIG. 7, the internal space of the second air bag 42 is pressurized by the continued driving of the pressure pump 32. Here, the air in the first air bag 41 is compressed by the second air bag 42. This increases the internal pressure of the first air bag 41 even in a state in which no air is supplied to the first air bag 41. In this way, the internal pressure of the first air bag 41 and the internal pressure of the second air bag 42 are increased.

During the process of increasing the internal pressure of the first air bag 41 and the internal pressure of the second air bag 42, a change in the internal pressure of the first air bag 41 is detected by the first pressure P1 sensor 31A1 and, on the basis of the detected pressure information, the calculation unit 25 in the control unit 20 calculates the blood pressure of the user.

As described above, in the first example, the pressure increase/reduction mechanism pressurizes the internal space of the first air bag 41 and, after the internal pressure of the first air bag 41 reaches the first pressure P1, the pressure increase/reduction mechanism pressurizes the internal space of the second air bag 42 while the first air bag 41 is kept sealed.

Specifically, by controlling the operation of the pressure pump 32 and the flow path switching valve 33, the internal space of the second air bag 42 is pressurized by the fluid supplied via the second air tube 62 after the internal space of the first air bag 41 is pressurized by the fluid supplied via the first air tube 61.

In this way, by pressurizing the internal space of the second air bag 42 while the first air bag 41 is kept sealed with the internal pressure having reached the first pressure P1, in accordance with Pascal's principle, even in a case of a small amount of air being supplied to the first air bag 41, the force of the first air bag 41 pressing against the measurement site can be amplified.

By reducing the amount of air supplied to the first air bag 41, pulse waves can be more clearly detected compared to a configuration in which only the first air bag 41 is inflated and the blood pressure information is measured. Thus, measurement accuracy can be improved.

Additionally, by the second air bag 42 being expanded after the first air bag 41 is expanded, the friction between the inner surface of the first air bag 41 and the outer surface of the second air bag 42 can be reduced when measuring blood pressure information compared to a configuration in which the second air bag 42 is expanded without the first air bag 41 being expanded. As a result, noise caused by friction can be suppressed, and noise superimposed on the detection value of the pressure sensor can be suppressed. Thus, measurement accuracy can be improved.

Figure 8:
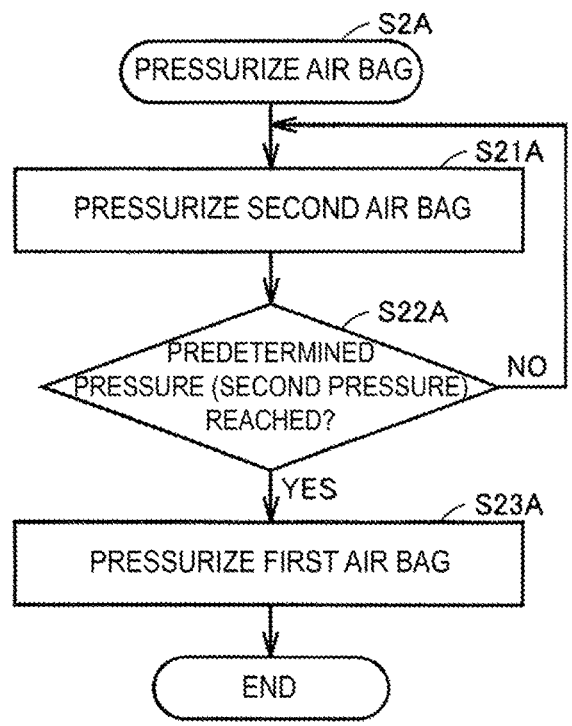
FIG. 8 is a flow chart illustrating a second example of the step of pressurizing the air bag indicated in FIG. 5.
Figure 9:
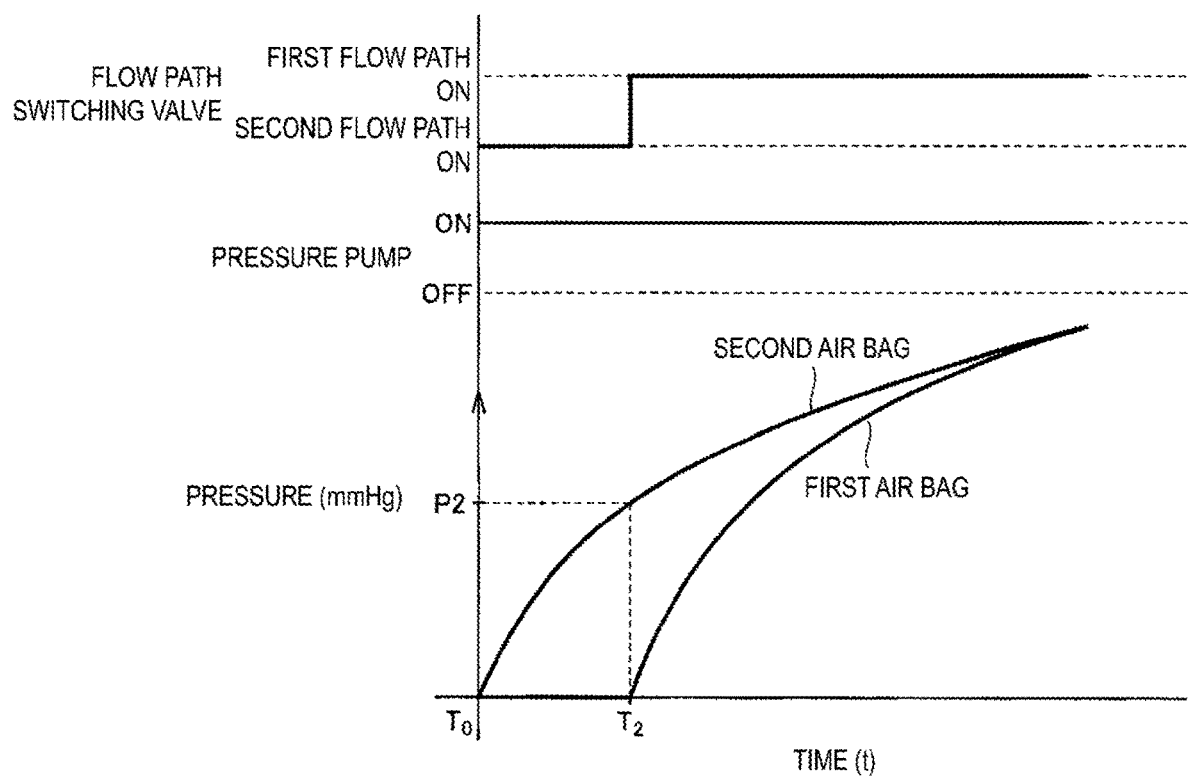
FIG. 9 is a diagram illustrating change in the operating state of a flow path switching valve and a pressure pump and change in the internal pressure of the first air bag and the second air bag, in accordance with the second example indicated in FIG. 8.

FIG. 8 is a flow chart illustrating a second example of the step of pressurizing the air bag indicated in FIG. 5. FIG. 9 is a diagram illustrating change in the operating state of the flow path switching valve and the pressure pump and change in the internal pressure of the first air bag and the second air bag, in accordance with of the second example indicated in FIG. 8. The second example of the step of pressurizing the air bag will be described with reference to FIGS. 8 and 9.

As illustrated in FIGS. 8 and 9, in the second example of the step of pressurizing the air bag (step S2A), firstly the second air bag 42 is pressurized (step S21A). Specifically, via the flow path switching valve 33, the first air tube 61 side is closed and the second air tube 62 and the pressure pump 32 are connected. This allows air to be supplied to the second air bag 42 via the second air tube 62. In this state, the pressure pump 32 is driven and air is supplied to the second air bag 42 via the second air tube 62, and the internal space of the second air bag 42 is pressurized.

Next, the control unit determines whether or not the internal pressure of the second air bag 42 has reached a predetermined pressure (the second pressure P2) on the basis of the pressure information of the second air bag 42 detected by the second pressure P2 sensor 31A2 (step S22A). Note that the second pressure P2 is greater than the first pressure P1.

In accordance with a determination that the internal pressure of the second air bag 42 is less than the predetermined pressure (NO in step S22A), pressurization of the internal space of the second air bag 42 continues until the internal pressure of the second air bag 42 reaches the second pressure P2.

In accordance with a determination that the internal pressure of the second air bag 42 has reached the second pressure P2 (YES in step S22A), the first air bag 41 is pressurized (step S23A). In the present embodiment, the pressurization of the internal space of the second air bag 42 starts at T0, and the internal pressure of the second air bag 42 reaches the second pressure P2 at T2.

In the step of pressurizing the first air bag 41, via the flow path switching valve 33, the second air tube 62 side is closed and the first air tube 61 and the pressure pump 32 are connected. This allows air to be supplied to the first air bag 41 via the first air tube 61. In this state, the second air bag 42 is kept sealed by the second exhaust valve 35 being kept in a closed state.

As illustrated in FIG. 9, the internal space of the first air bag 41 is pressurized by the continued driving of the pressure pump 32. Here, while air is being supplied to the first air bag 41, the air in the first air bag 41 is compressed by the second air bag 42 expanded earlier. This increases the internal pressure of the first air bag 41 with a smaller amount of supplied air than a configuration in which only the first air bag 41 is expanded.

In this configuration, the internal pressure of the first air bag 41 is increased and the internal pressure of the second air bag 42 is increased. During the process of increasing the internal pressure of the first air bag 41 and the internal pressure of the second air bag 42, a change in the internal pressure of the first air bag 41 is detected by the first pressure P1 sensor 31A1 and, on the basis the detected pressure information, the calculation unit 25 in the control unit 20 calculates the blood pressure of the user.

As described above, in the second example, the pressure increase/reduction mechanism pressurizes the internal space of the second air bag 42 and, after the internal pressure of the second air bag 42 reaches the second pressure P2, the pressure increase/reduction mechanism pressurizes the internal space of the first air bag 41 while the second air bag 42 is kept sealed.

Specifically, by controlling the operation of the pressure pump 32 and the flow path switching valve 33, the internal space of the first air bag 41 is pressurized by the fluid supplied via the first air tube 61 after the internal space of the second air bag 42 is pressurized by the fluid supplied via the second air tube 62.

In this way, by pressurizing the internal space of the first air bag 41 while the second air bag 42 is kept sealed with the internal pressure having reached the second pressure P2, in accordance with Pascal's principle, even in a case of a small amount of air being supplied to the first air bag 41, the force of the first air bag 41 pressing against the measurement site can be amplified.

By reducing the amount of air supplied to the first air bag 41, pulse waves can be more clearly detected compared to a configuration in which only the first air bag 41 is inflated and the blood pressure information is measured. Thus, measurement accuracy can be improved.

Additionally, by the first air bag 41 being expanded after the second air bag 42 is expanded, the friction between the inner surface of the first air bag 41 and the outer surface of the second air bag 42 can be reduced when measuring blood pressure information compared to a configuration in which the second air bag 42 is expanded without the first air bag 41 being expanded. As a result, noise caused by friction can be suppressed, and noise superimposed on the detection value of the pressure sensor can be suppressed. Thus, measurement accuracy can be improved.

Note that, in the first embodiment, a configuration has been described in which the second pressure P2 sensor 31A2 is provided to detect the internal pressure of the second air bag 42, but no such limitation is intended. In another configuration, when the blood pressure information is measured according to the second example of the step of pressurizing the air bag described above, the internal pressure of the first air bag 41 can be measured by the second pressure P2 sensor 31A2 even in a case where a state is switched to the second state by the flow path switching valve 33. Thus, the first pressure P1 sensor 31A1 and the oscillation circuit 51A1 can be omitted. In this configuration, the second pressure P2 sensor 31A2 corresponds to the pressure detection device.

Second Embodiment

Figure 10:
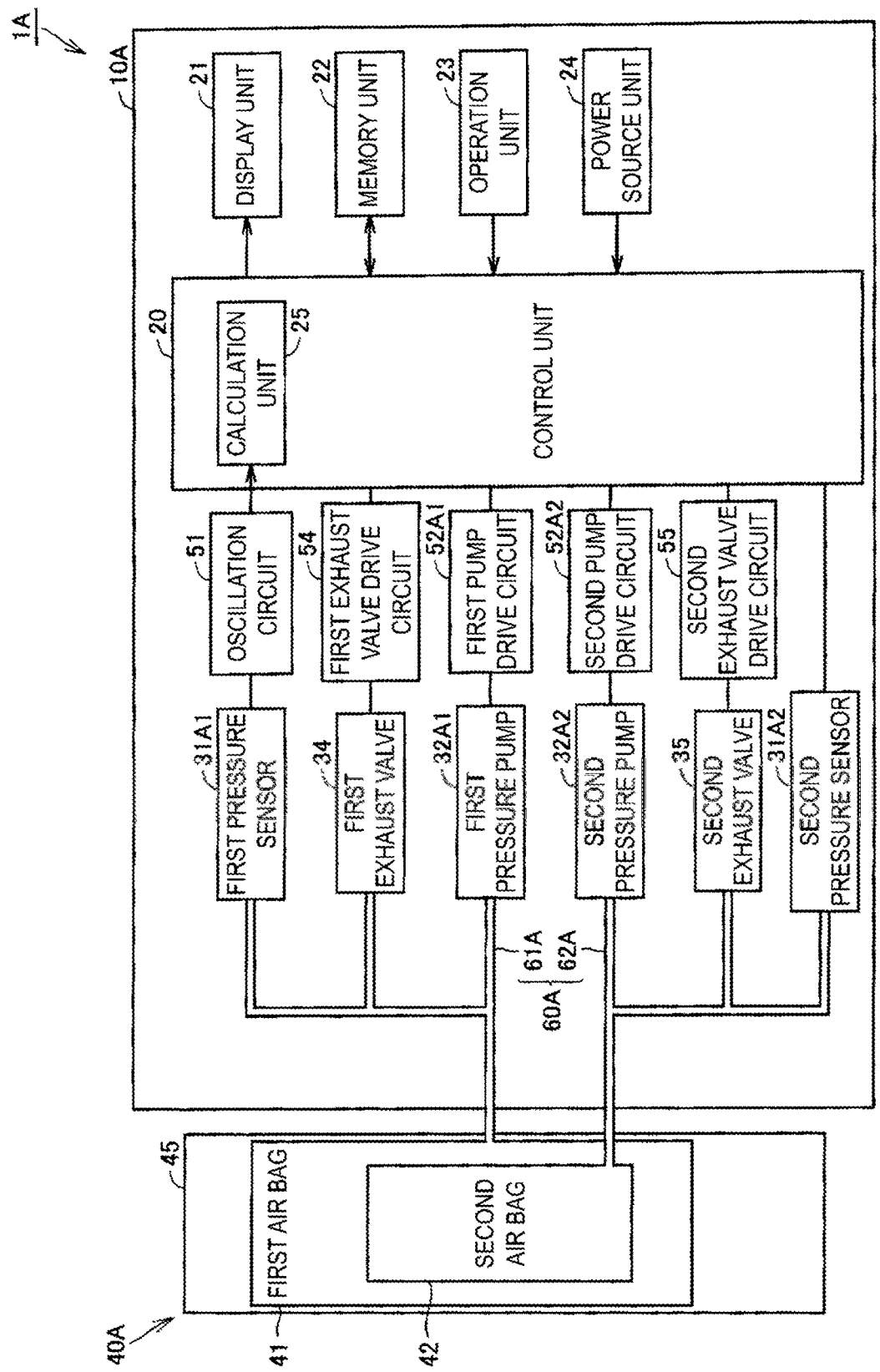
FIG. 10 is a functional block diagram illustrating the configuration of a blood pressure monitor according to a second embodiment.

FIG. 10 is a functional block diagram illustrating the configuration of the blood pressure monitor according to a second embodiment. A blood pressure monitor 1A according to the second embodiment will be described with reference to FIG. 10.

As illustrated in FIG. 10, the blood pressure monitor 1A according to the second embodiment differs from the blood pressure monitor 1 according to the first embodiment in that the flow path switching valve 33 is not provided and the first air bag 41 and the second air bag 42 are pressurized using flow paths and pumps that are independent of each other.

Specifically, the blood pressure monitor 1A according to the second embodiment differs from the blood pressure monitor 1 according to the first embodiment in that the configurations of an air tube 60A and a body 10A are different. Note that the configuration of the cuff 40 according to the second embodiment is substantially the same as that of the first embodiment.

The air tube 60A is constituted by a first air tube 61A and a second air tube 62A independent of each other. A distal end of the first air tube 61A is connected to the first nipple 43 of the first air bag 41, and a base end of the first air tube 61A is connected to a first pressure pump 32A1, which will be described later. A distal end of the second air tube 62A is connected to the second nipple 44 of the second air bag 42, and a base end of the second air tube 62A is connected to a second pressure pump 32A2, which will be described later.

The body 10A is mainly different from the body 10 according to the first embodiment in that the first pressure pump 32A1 that pressurizes the internal space of the first air bag 41 and the second pressure pump 32A2 that pressurizes the internal space of the second air bag 42 are provided independently.

The first pressure pump 32A1 supplies air to the first air bag 41 via the first air tube 61A. The second pressure pump 32A2 supplies air to the second air bag 42 via the second air tube 62A.

The body 10A includes a first pump drive circuit 52A1 that drives the first pressure pump 32A1 and a second pump drive circuit 52A2 that drives the second pressure pump 32A2. The first pump drive circuit 52A1 and the second pump drive circuit 52A2 respectively control operations of the first pressure pump 32A1 and the second pressure pump 32A2 on the basis of an input signal from the control unit 20.

The body 10A also includes a first pressure P1 sensor 31A1 that measures the internal pressure of the first air bag 41 and a second pressure P2 sensor 31A2 that measures the internal pressure of the second air bag 42.

In the present embodiment, the first pressure pump 32A1, the first exhaust valve 34, the second pressure pump 32A2, and the second exhaust valve 35 correspond to a pressure increase/reduction mechanism that increases or decreases the pressure in the internal space of the first air bag 41 and the second air bag 42. That is, the pressure increase/reduction mechanism includes the first pressure pump 32A1 that pressurizes the first air bag 41 and the second pressure pump 32A2 that pressurizes the second air bag 42.

The pressure increase/reduction mechanism is configured to be switchable from a first state to a second state. In the first state, the one fluid bag of the first air bag 41 and the second air bag 42 is pressurized and expanded. In the second state, the one fluid bag of the first air bag 41 and the second air bag 42 is kept sealed and the other fluid bag of the first air bag 41 and the second air bag 42 is pressurized and expanded.

In the blood pressure monitor 1A according to the second embodiment, blood pressure information is measured in accordance with the measurement method according to the first embodiment. Specifically, similar operations as those in step S1 to step S5 are performed in the same manner as in the first embodiment.

In step S2, as in the first embodiment, the operation according to the first or second example of the step of pressurizing the air bag is performed.

Figure 11:
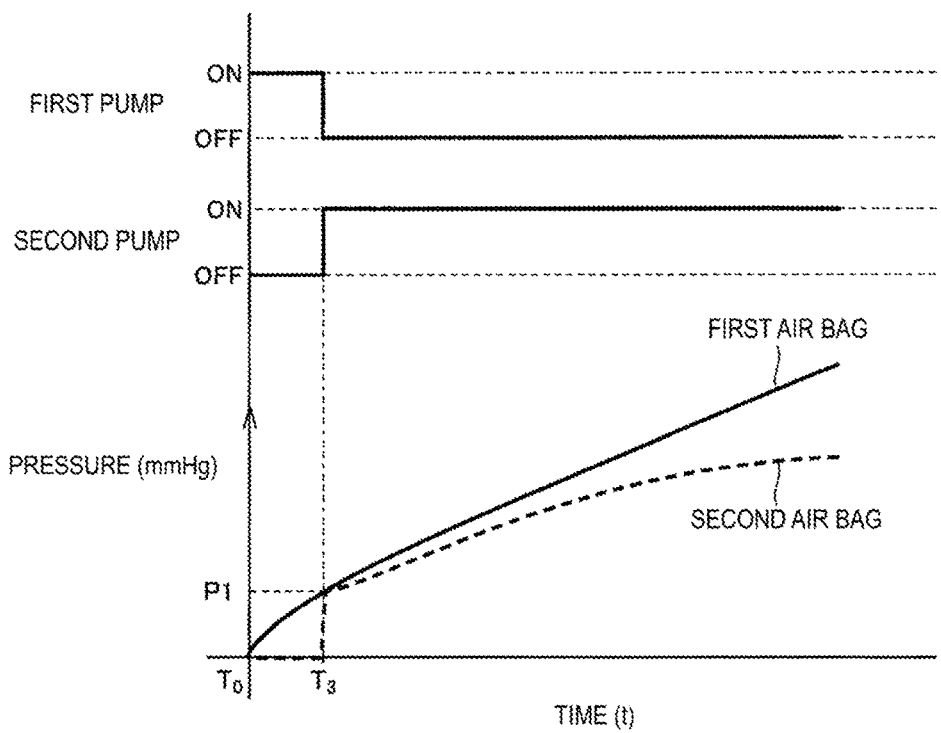
FIG. 11 is a diagram illustrating change in the operating state of a first pressure pump and a second pressure pump and change in the internal pressure of the first air bag and the second air bag, in accordance with a first example of the step of pressurizing the air bag according to the second embodiment.

FIG. 11 is a diagram illustrating change in the operating state of the first pressure pump and the second pressure pump and change in the internal pressure of the first air bag and the second air bag in accordance with the first example of the step of pressurizing the air bag according to the second embodiment.

As illustrated in FIG. 11, when the operation according to the first example of the step of pressurizing the air bag is performed, the first pressure pump 32A1 is driven with the second pressure pump 32A2 being stopped. In this way, air is supplied to the first air bag 41 via the first air tube 61A, and the first air bag 41 is pressurized.

Next, the control unit determines whether or not the internal pressure of the first air bag 41 has reached a predetermined pressure (the first pressure P1) on the basis of the pressure information of the first air bag 41 detected by the first pressure P1 sensor 31A1. In accordance with a determination that the internal pressure of the first air bag 41 is less than the predetermined pressure, pressurization of the first air bag 41 continues until the internal pressure of the first air bag 41 reaches the first pressure P1.

In accordance with a determination that the internal pressure of the first air bag 41 has reached the first pressure P1, the second air bag 42 is pressurized. In the present embodiment, the pressurization of the internal space of the first air bag 41 starts at T0, and the pressure of the first air bag 41 reaches the first pressure P1 at T3.

In the step of pressurizing the second air bag 42, the second pressure pump 32A2 is driven with the first pressure pump 32A1 being stopped. Here, the first air bag 41 can be kept sealed by the first exhaust valve 34 being kept in a closed state.

As illustrated in FIG. 11, the internal space of the second air bag 42 is pressurized by the driving of the second pressure pump 32A2. Here, the air in the first air bag 41 is compressed by the second air bag 42. This increases the internal pressure of the first air bag 41 even in a state in which no air is supplied to the first air bag 41.

During this process of increasing the internal pressure of the first air bag 41 and the internal pressure of the second air bag 42, a change in the internal pressure of the first air bag 41 is detected by the first pressure P1 sensor 31A1 and, on the basis of the detected pressure information, the calculation unit 25 in the control unit 20 calculates the blood pressure of the user.

As described above, in the operation according to the first example of the step of pressurizing the air bag, the pressure increase/reduction mechanism pressurizes the internal space of the first air bag 41 and, after the internal pressure of the first air bag 41 reaches the first pressure P1, the pressure increase/reduction mechanism pressurizes the internal space of the second air bag 42 while the first air bag 41 is kept sealed.

Specifically, after the control unit 20 drives the first pressure pump 32A1 with the second pressure pump 32A2 being stopped, the control unit 20 controls the operation of the pressure increase/reduction mechanism so as to drive the second pressure pump 32A2 with the first pressure pump 32A1 being stopped.

In this case as well, as in the first embodiment, the amount of air supplied to the first air bag 41 can be reduced, allowing the pulse waves to be clearly detected. As a result, measurement accuracy can be improved. Additionally, noise caused by friction between the first air bag 41 and the second air bag 42 can be suppressed, and noise superimposed on the detection value of the pressure sensor can be suppressed. Thus, measurement accuracy can be improved.

Figure 12:
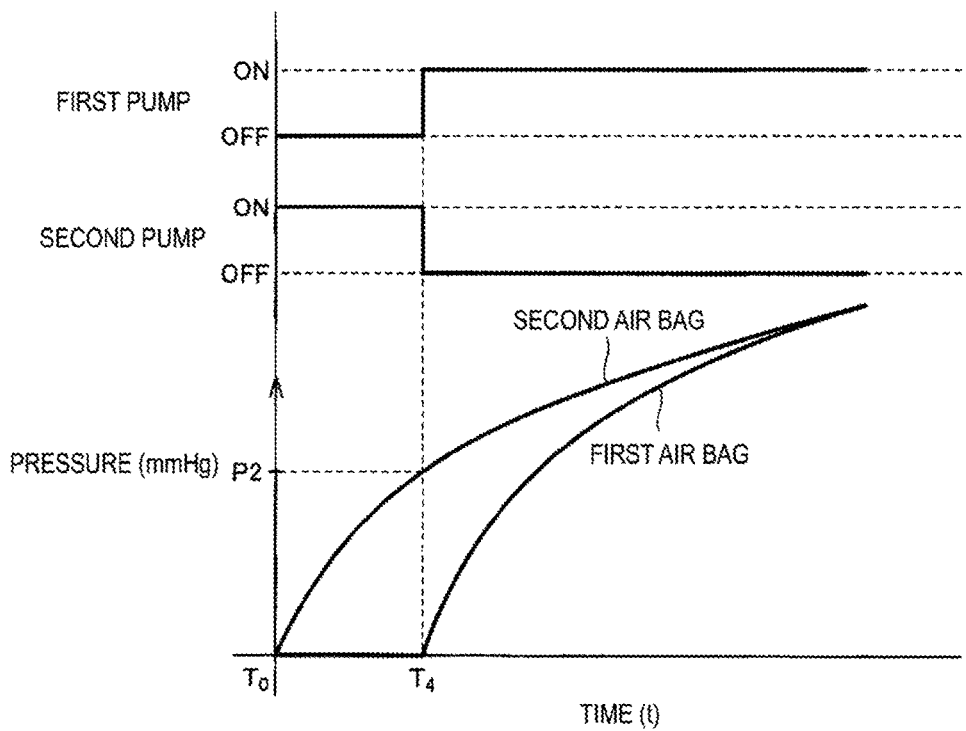
FIG. 12 is a diagram illustrating change in the operating state of a first pressure pump and a second pressure pump of a second example and change in the internal pressure of the first air bag and the second air bag, in accordance with the step of pressurizing the air bag according to the second embodiment.

FIG. 12 is a diagram illustrating change in the operating state of the first pressure pump and the second pressure pump and change in the internal pressure of the first air bag and the second air bag in accordance with a second example of the step of pressurizing the air bag according to the second embodiment.

As illustrated in FIG. 12, when the operation according to the second example of the step of pressurizing the air bag is performed, the second pressure pump 32A2 is driven with the first pressure pump 32A1 being stopped. In this way, air is supplied to the second air bag 42 via the second air tube 62A, and the second air bag 42 is pressurized.

Next, the control unit determines whether or not the internal pressure of the second air bag 42 has reached a predetermined pressure (the second pressure P2) on the basis of the pressure information of the second air bag 42 detected by the second pressure P2 sensor 31A2. In accordance with a determination that the internal pressure of the second air bag 42 is less than the predetermined pressure, pressurization of the second air bag 42 continues until the internal pressure of the second air bag 42 reaches the second pressure P2.

In accordance with a determination that the internal pressure of the second air bag 42 has reached the second pressure P2, the first air bag 41 is pressurized. In the present embodiment, the pressure of the second air bag 42 starts at T0, and the pressure of the second air bag 42 reaches the second pressure P2 at T4.

In the step of pressurizing the first air bag 41, the first pressure pump 32A1 is driven with the second pressure pump 32A2 being stopped. Here, the second air bag 42 can be kept sealed by the second exhaust valve 35 being kept in a closed state.

As illustrated in FIG. 12, the first air bag 41 is pressurized by the driving of the first pressure pump 32A1. Here, while air is being supplied to the first air bag 41, the air in the first air bag 41 is first compressed by the second air bag 42. This increases the internal pressure of the first air bag 41 with a smaller amount of supplied air than a configuration in which only the first air bag 41 is expanded.

In this configuration, the internal pressure of the first air bag 41 is increased and the internal pressure of the second air bag 42 is increased. During the process of increasing the internal pressure of the first air bag 41 and the internal pressure of the second air bag 42, a change in the internal pressure of the first air bag 41 is detected by the first pressure P1 sensor 31A1 and, on the basis of the detected pressure information, the calculation unit 25 in the control unit 20 calculates the blood pressure of the user.

As described above, in the operation according to the second example of the step of pressurizing the air bag, the pressure increase/reduction mechanism pressurizes the internal space of the second air bag 42 and, after the internal pressure of the second air bag 42 reaches the second pressure P2, the pressure increase/reduction mechanism pressurizes the internal space of the first air bag 41 while the second air bag 42 is kept sealed.

Specifically, after the control unit 20 drives the second pressure pump 32A2 with the first pressure pump 31A1 being stopped, the control unit 20 controls the operation of the pressure increase/reduction mechanism so as to drive the first pressure pump 32A1 with the second pressure pump 32A2 being stopped.

In this case as well, as in the first embodiment, the amount of air supplied to the first air bag 41 can be reduced, allowing the pulse waves to be clearly detected. As a result, measurement accuracy can be improved. Additionally, noise caused by friction between the first air bag 41 and the second air bag 42 can be suppressed, and noise superimposed on the detection value of the pressure sensor can be suppressed. Thus, measurement accuracy can be improved.

Modified Example

Figure 13:
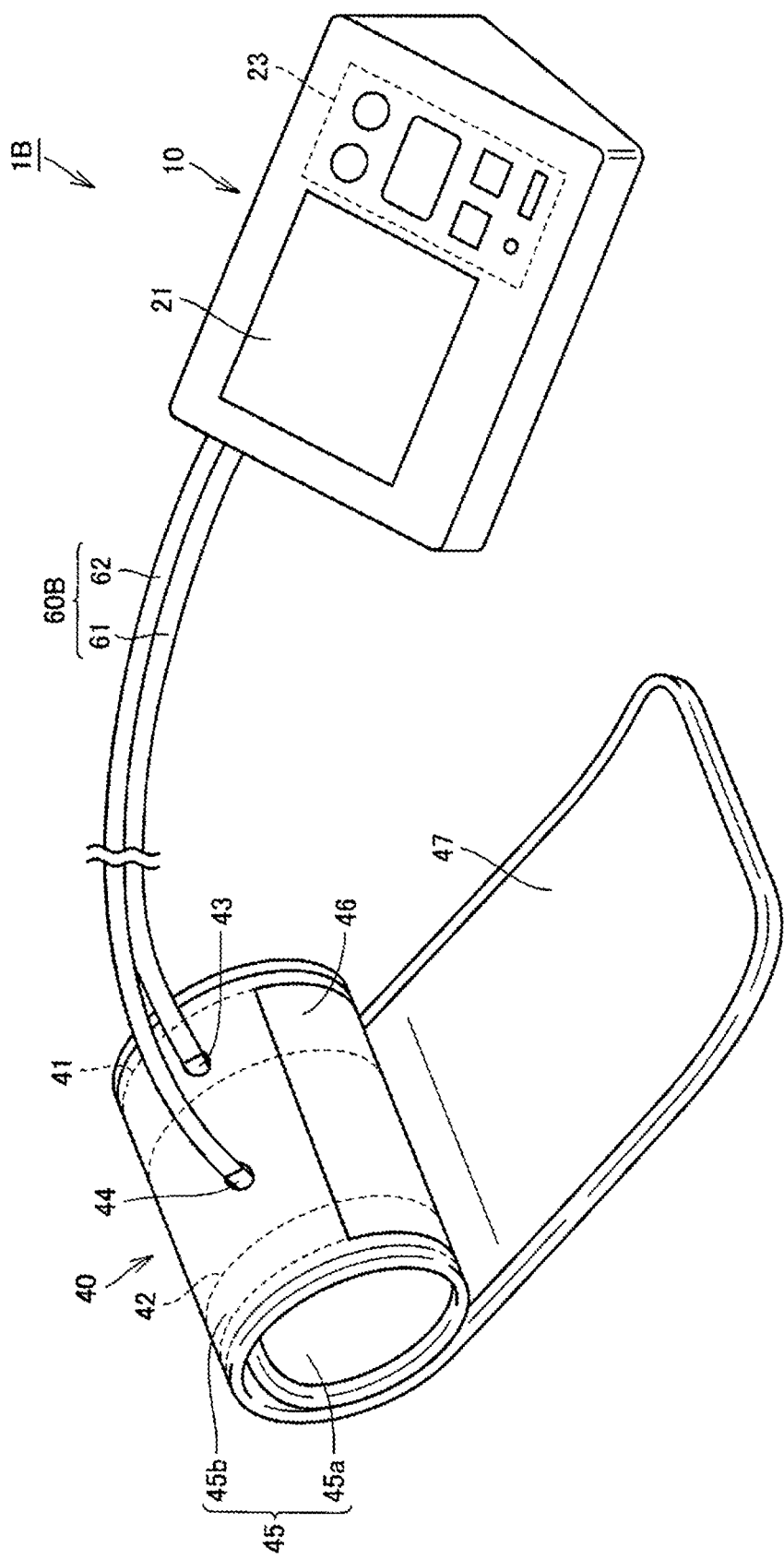
FIG. 13 is a perspective view illustrating an appearance and a structure of a blood pressure monitor according to a modified example.

FIG. 13 is a perspective view illustrating an appearance and a structure of a blood pressure monitor according to a modified example. The appearance and the structure of the blood pressure monitor according to the modified example will be described with reference to FIG. 13.

As illustrated in FIG. 13, the blood pressure monitor 1B according to the modified example differs from the blood pressure monitor 1 according to the first embodiment in that the configuration of an air tube 60B is different. Other configurations are substantially similar. The first air tube 61 and the second air tube 62 of the air tube 60B are formed together on the body 10 side. Specifically, on the body 10 side, a trunk section of the first air tube 61 and a trunk section of the second air tube 62 are connected, and the first air tube 61 and the second air tube 62 have a multi-trunk structure. On the first nipple 43 and the second nipple 44 side, the first air tube 61 and the second air tube 62 are branched off from one another. The air tube 60B may be configured in this manner. In the blood pressure monitor 1B according to the modified example, blood pressure can be measured via a measurement flow substantially similar to that of the first embodiment.

Note that the configuration of the air tube 60B of the blood pressure monitor 1B can naturally be applied to the blood pressure monitor 1A according to the second embodiment.

In the first embodiment, the second embodiment, and the modified example described above, a pressure measurement method is employed as the measurement method, but no such limitation is intended. A pressure reduction measurement method in which pulse waves are detected when the pressure of the first air bag 41 and the second air bag 42 is decreased may naturally be employed.

In the first embodiment, the second embodiment, and the modified example described above, an air bag in which air can enter and exit has been used as the fluid bag, but no such limitation is intended. A bag in which a gas other than air or a non-compressible viscous fluid other than air enters and exits can also be used. In other words, in the embodiment described above, compressed air is used as the flow-controlled fluid, but application of the contents described above is not limited thereto. A high-pressure gas other than compressed air, a liquid in a compressed environment, or the like may be used as the flow-controlled fluid.

Embodiments of the present invention have been described above, but the embodiments described herein are illustrative in all respects and are not intended as limitations. The scope of the present invention is indicated by the claims and includes all meaning equivalent to the scope and changes within the scope.

REFERENCE SIGNS LIST 1, 1A, 1B Blood pressure monitor
10, 10A Body
20 Control unit
21 Display unit
22 Memory unit
23 Operation unit
24 Power source unit
25 Calculation unit
31A1 First pressure P1 sensor
31A2 Second pressure P2 sensor
32 Pressure pump
32A1 First pressure pump
32A2 Second pressure pump
33 Flow path switching valve
34 First exhaust valve
35 Second exhaust valve
40 Cuff
41 First air bag
41a, 41b Outer surface
41c, 41d Inner surface
42 Second air bag
42a, 42b Outer surface
42c, 42d Inner surface
43 First nipple
44 Second nipple
45 Outer cover
45a Inner cover member
45b Outer cover member
46, 47 Surface fastener
51A1, 51A2 Oscillation circuit
52 Pressure pump drive circuit
52A1 First pump drive circuit
52A2 Second pump drive circuit
53 Switching valve drive circuit
54 First exhaust valve drive circuit
55 Second exhaust valve drive circuit
60, 60A, 60B Air tube
61, 61A First air tube
62, 62A Second air tube

The invention claimed is:

1. A blood pressure information measurement device comprising:
  a cuff comprising
    a first fluid bag configured to expand and contract by a fluid entering and exiting a first nipple of the first fluid bag, and
    a second fluid bag accommodated in the first fluid bag and configured to expand and contract by a fluid entering and exiting a second nipple of the second fluid bag, wherein the first nipple is disposed at a position corresponding to an outer edge section of the second fluid bag or a position further outward than the outer edge section;
  a pressure increase/reduction mechanism configured to increase and decrease an internal pressure in an internal space of the first fluid bag and an internal pressure in an internal space of the second fluid bag;
  a control unit configured to control operation of the pressure increase/reduction mechanism;

a pressure detection device configured to detect the internal pressure of the first fluid bag and the internal pressure of the second fluid bag; and a calculation unit configured to calculate blood pressure on the basis of pressure information detected by the pressure detection device with the cuff being worn at a measurement site; wherein the control unit controls the operation of the pressure increase/reduction mechanism such that, in a first stage, the internal space of the first fluid bag is pressurized and expanded until the internal pressure of the first fluid bag reaches a predetermined pressure, and, in a second stage which begins immediately after the first stage, the internal space of the second fluid bag is pressurized and expanded while the first fluid bag is kept sealed, so that in the second stage the internal pressure of the internal space of the first fluid bag and the internal pressure of the internal space of the second fluid bag are increased, wherein the control unit begins the second stage upon determining that the internal pressure of the first fluid bag reaches the predetermined pressure, the calculation unit calculates the blood pressure using the internal pressure of the first fluid bag as detected by the pressure detection device during the second stage, the first fluid bag being kept sealed during the entire second stage, and the blood pressure is calculated during the expansion of the second fluid bag.

2. The blood pressure information measurement device according to claim 1, wherein the pressure increase/reduction mechanism comprises a first pressure pump and a second pressure pump, the first pressure pump pressurizes the internal space of the first fluid bag, the second pressure pump pressurizes the internal space of the second fluid bag, and the control unit, after the first pressure pump is driven with the second pressure pump being stopped, controls operation of the pressure increase/reduction mechanism to drive the second pressure pump with the first pressure pump being stopped.

3. The blood pressure information measurement device according to claim 1, wherein the pressure increase/reduction mechanism comprises a single pressure pump, a fluid supply path, and a switching valve, the pressure pump pressurizes the internal space of the first fluid bag and the internal space of the second fluid bag, an end on a first side of the fluid supply path is connected to the pressure pump, an end on a second side of the fluid supply path branches into a first supply path connected to the first fluid bag and a second supply path connected to the second fluid bag, the switching valve is provided at a point along the fluid supply path and switches between a state in which a fluid is supplied to the first fluid bag via the first supply path and a state in which a fluid is supplied to the second fluid bag via the second supply path, and the control unit, by controlling operation of the pressure pump and the switching valve, pressurizes the internal space of the second fluid bag via the fluid supplied via the second supply path, after the internal space of the first fluid bag is pressurized via the fluid supplied via the first supply path.

4. The blood pressure information measurement device according to claim 1, wherein the control unit determines whether the internal pressure of the first fluid bag reaches the predetermined pressure on a basis of pressure information detected by the pressure detection device.

\* \* \* \* \*